(12) United States Patent
Nakagaki et al.

(10) Patent No.: US 6,451,327 B1
(45) Date of Patent: Sep. 17, 2002

(54) SKIN CLEANSING COMPOSITION

(75) Inventors: Kiyoko Nakagaki; Masaaki Moriyama; Hiroe Tanahashi; Tomoko Umezawa; Hideyuki Hanazawa, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/465,445

(22) Filed: Dec. 17, 1999

(30) Foreign Application Priority Data

Dec. 28, 1998 (JP) .......................................... 10-374239

(51) Int. Cl.⁷ ............................. A61K 7/00; A61K 9/00; A61K 9/14; A61K 9/16
(52) U.S. Cl. ...................... 424/401; 424/400; 424/489; 424/490; 424/493; 424/494
(58) Field of Search ................................. 424/400, 401, 424/489, 490, 493, 494, 495, 496, 497

(56) References Cited

U.S. PATENT DOCUMENTS 3,975,280 A * 8/1976 Hachmann et al. ......... 252/102
5,206,019 A * 4/1993 Nichols

FOREIGN PATENT DOCUMENTS

| EP | 0 104 679 A | 4/1984 |
| FR | 2 779 650 A | 12/1999 |
| GB | 2 158 839 A | 11/1985 |
| WO | WO 97 38078 A | 10/1997 |

OTHER PUBLICATIONS

Database WPI Section Ch, Week 198551 Derwent Publications Ltd., London, GB; Class D21, AN 1985–319455 XP002154147 & JP 60 221499 A (Shiseido Co Ltd), Nov. 6, 1985.

Patent Abstracts of Japan, vol. 1998 No. 10, Aug. 31 1998 JP 10 120552 a (Shiseido Co Ltd), May 12, 1998.

* cited by examiner

Primary Examiner—Thurman K. Page
Assistant Examiner—S. Tran
(74) Attorney, Agent, or Firm—Oblon, Spivak, McClelland, Maier & Neustadt, P.C.

(57) ABSTRACT

The invention relates to a substantially nonaqueous skin cleansing composition comprising a granulated product obtained by granulating particles of a surfactant selected from the group consisting of nonionic surfactants, amphoteric surfactants and anionic surfactants with a binder. The composition scarcely causes damage to and itch on the skin, can give an effective massaged feeling and has excellent cleanability.

13 Claims, No Drawings

SKIN CLEANSING COMPOSITION

BACKGROUND OF THE INVENTION

1. Field of the Invention

The present invention relates to a skin cleansing composition which can give an effective massaged feeling and has excellent cleanability.

2. Description of the Background Art

There are massaging compositions having as its objects the facilitation of the circulation of blood and the removal of an aged horny layer by the physical irritation of a scrubber, and detergent compositions having a physical cleansing effect that dirt or smears filled in pores of the skin are removed by a scrubber. The scrubber is generally composed of a water-insoluble substance such as a ground product of plant seeds, beads of a synthetic resin such as polyethylene, or an oily substance which is solid at an ordinary temperature, and is generally dispersed in a water-soluble base. However, such a water-insoluble scrubber has involved problems that it is poor in usability by reasons of difficult removal after use according to the particle diameter thereof and the like and that a sufficient massaging effect cannot be achieved.

In order to facilitate the removal after use, there has been proposed a granule-blended cosmetic composition in which granules of crystals of a saccharide or sugaralcohol, which is easily water-soluble, are dispersed in hydrophilic nonaqueous gel (Japanese Patent Application Laid-Open No. 17591911989. However, the composition is required to be washed out with a detergent or the like because it gives a feeling of remaining after use and is sticky to the feel.

SUMMARY OF THE INVENTION

It is an object of the present invention to provide a skin cleansing composition which can give an effective massaged feeling and has excellent cleanability.

The present inventors have found that a cleansing composition with a granulated product obtained by granulating particles of a specific surfactant with a binder incorporated into a substantially nonaqueous base can give an effective massaged feeling, and moreover has excellent cleanability and is easy to remove because the granulated product functions as a surfactant by physical disintegration or disintegration by contact with water, thus leading to completion of the present invention.

According to the present invention, there is provided a substantially nonaqueous skin cleansing composition comprising a granulated product obtained by granulating particles of a surfactant selected from the group consisting of nonionic surfactants, amphoteric surfactants and anionic surfactants with a binder.

The substantially nonaqueous skin cleansing composition according to the present invention scarcely causes damage to and itch on the skin, can give an effective massaged feeling and has excellent cleanability and no feeling of remaining after use.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

As particles of the surfactant for forming the granulated product useful in the practice of the present invention, there may be used crystals or powder of a nonionic surfactant, amphoteric surfactant or anionic surfactant.

Examples of the nonionic surfactant include polyoxyethylene fatty acid esters, polyoxyethylene hardened castor oil, polyoxyethylene sorbitan fatty acid esters, glycerol fatty acid esters, polyoxyethylene alkyl ethers, polyoxyethylene polyoxypropylene glycol and alkylsaccharide type surfactants, with polyoxyethylene glycol monostearate,-polyoxyethylene lauryl ether, polyoxyethylene (160) polyoxypropylene (30) glycol, alkylpolyglycosides, etc. being particularly preferred.

Examples of the amphoteric surfactant include carbobetaine type surfactants, amidobetaine type surfactants, sulfobetaine type surfactants, phosphobetaine type surfactants, imidazolinium betaine type surfactants and amine oxide type surfactants, with fatty acid amide propylbetaines, alkylhydroxysulfobetaines, 2-alkyl-N-carboxymethyl-N-hydroxyethyl-imidazolinium betaines, alkyldimethylamine oxides, etc. being particularly preferred.

Examples of the anionic surfactant include higher fatty acid salts, polyoxyethylene alkyl ether sulfates, polyoxyethylene alkyl ether carboxylates, alkyl ether carboxylates, alkylsulfates, alkylbenzenesulfonates, higher fatty acid ester sulfonates, acylated isethionates, acylated amino acid salts, alkylisethionates, alkylphosphates, alkylsulfonates, N-acylamino acid salts, N-acyl-carboxyalkylglycine salts, N-alkylamidoalkanol sulfates and N-acyl-N-alkyltaurine salts. Of these, higher fatty acid salts, N-lauroyl-β-alanine salts, monoalkylphosphates, higher fatty acid ester sulfonates, acylated isethionates, polyoxyethylene lauryl sulfates, lauryl sulfates, myristyl sulfates and polyoxyethylene laurylamide acetate are preferred.

Incidentally, as the salt used herein, is referred a salt with a metal such as potassium, sodium or magnesium, an ammonium salt, or an organic ammonium salt such as a monoethanol ammonium salt.

The particles of the surfactants are preferably those having a particle diameter of 0.01 to 1,000 $\mu$m, particularly 0.01 to 700 $\mu$m. The particles of the surfactants may be used either singly or in any combination thereof and preferably comprise an anionic surfactant, particularly, a higher fatty acid sodium salt, potassium N-lauroyl-β-alanine, sodium monoalkylphosphate or sodium coconut oil fatty acid ethyl ester sulfonate.

As the binder used for granulating the surfactant, a water-soluble or a water-insoluble binder is used.

No particular limitation is imposed on the water-soluble binder so far as it dissolves upon contact with water. Examples thereof include synthetic polymers such as polyvinyl alcohol derivatives, poly(meth)acrylic acid alkali salts, alkali salts of (meth)acrylic acid/(meth)acrylic ester copolymers, alkali salts of acrylic acid/maleic acid copolymers and polyvinyl pyrrolidone; semisynthetic polymers such as starch derivatives, ethyl cellulose, methyl cellulose, carboxymethyl cellulose and hydroxyalkyl cellulose; and natural polymers derived from starch, see weeds, plant mucilages, proteins, etc.

Examples of the water-insoluble binder include acetyl cellulose, nitrocellulose, bentonite, talc, kaolin, silica, calcium carbonate, titaniumoxide, silicic acid anhydride, hydroxycalcium apatite, pearly substance and vinyl acetate resins.

The water-soluble binder is preferred. as the binder, with a polyvinyl alcohol derivative, ethyl cellulose or methyl cellulose being particularly preferred.

The binders may be used either singly or in any combination thereof in a proportion of preferably 0.1 to 80 parts by weight, particularly 0.5 to 70 parts by weight per 100 parts by weight of the surfactant particles.

No particular limitation is imposed on a method for granulating the surfactant particles with the binder. For example, they can be prepared by following a granulation process such as rolling granulation, rolling fluidized granulation, fluidized bed granulation, agitated rolling granulation, melt granulation, extrusion granulation or spray granulation, or a coating process such as spray drying after mixing the surfactant particles and the binder or while mixing them.

Into the granulated product, may be incorporated an oily substance which is solid at an ordinary temperature, for example, sunflower oil, a vegetable oil such as olive oil, silicone oil, volatile silicone oil, hardened castor oil, and/or the like in addition to the surfactant particles and binder.

The particle diameter of the thus-obtained granulated product is preferably 10 to 10,000 μm, particularly 100 to 5,000 μm from the viewpoint of the massaging effect. The granulated product is preferably incorporated in a proportion of 0.5 to 60% by weight, particularly 1 to 40% by weight, more particularly 2 to 30% by weight based on the total weight of the composition.

The skin cleansing composition according to the present invention must be nonaqueous, i.e., is required to substantially contain no water. However, it is unavoidable that water is mixed into the composition to some extent when water is contained in raw materials used. The term "substantially nonaqueous" as used in the present invention means that a water content in the composition is preferably 10% by weight or lower, particularly 7% by weight or lower.

The skin cleansing composition according to the present invention is prepared by incorporating the granulated product into a nonaqueous base. The nonaqueous base is preferably liquid at ordinary temperature and pressure. Examples thereof include ethylene glycol monoethyl ether (ethylcarbitol), isoprene glycol, hexylene glycol, 1,2-pentanediol, polyethylene glycol, dipropylene glycol, ethylene glycol monobutyl ether, ethylene glycol monoethyl ether, 1,3-butylene glycol, 2-ethyl-1,3-hexanediol, diethylene glycol, propylene glycol and tris(ethoxyethoxyethyl) phosphate, with diethylene glycol monoethyl ether, isoprene glycol, hexylene glycol, dipropylene glycol, 1,3-butylene glycol and tris(ethoxyethoxyethyl)phosphate being particularly preferred.

These bases may be used either singly or in any combination thereof and preferably incorporated in a proportion of 40 to 99.5 % by weight, particularly 60 to 99% by weight based on the total weight of the composition from the viewpoints of a feeling upon use and a massaging effect.

Into the skin cleansing composition according to the present invention, may be suitably incorporated surfactants, antioxidants, germicides, antiphlogistics, oily substances, medicinally-effective ingredients, cold sensation-imparting agents, preservatives, perfume bases; inorganic powder such as talc, kaolin. pearly substances, hydroxycalcium apatite, silica, calcium carbonate, titanium oxide and silicic acid anhydride; thickeners such as hydroxypropyl cellulose and polyvinyl pyrrolidone; etc. in addition to the above-described components.

When the water-soluble binder is used as the binder in the granulated product used in the present invention, the granulated product is disintegrated by contact with water. When the water-insoluble-binder is used on the other hand, the granulated product is disintegrated by physical force, i.e., massaging. In each case, the cleansing function by the surfactant particles is exhibited after the disintegration of the granulated product, and so excellent cleanability can be achieved.

When the granulated product is disintegrated by the physical force, an end point of massaging can be identified by the time the granulated product has been disintegrated, and so it is only necessary to wash out the composition by adding water after that.

EXAMPLE 1

Sodium coconut oil fatty acid ethyl ester sulfonate (200 g), starch (120 g) and purified water (200 g) were mixed and kneaded while heating them to about 50 to 60° C. in a container. The mixture was uniformly placed on a metallic tray of 30 cm×25 cm and left to stand for about 2 days in a dryer (about 55° C.) to dry it so as to give a water content of 4% or lower. The dried product was ground for about 10 to 20 seconds by a grinder (MK-K75; manufactured by National Co.), and the ground product was sifted by sieves of 850 μm and 500 μm. Particles remaining on the sieves were provided as a granulated product (particle diameter: 500 to 900 μm) of a surfactant. On the other hand, an acrylic acid-alkyl methacrylate copolymer (Carbopol ETD-2020, product of B.F. Goodrich Company; 2 g) was mixed into a mixture of polyethylene glycol 400 (product of Sun Chemical Co., Ltd.; 150 g) and glycerol (20 g) with stirring to prepare a nonaqueous base. The granulated product of the surfactant (25 g) was mixed with the base to obtain a substantially nonaqueous skin cleansing composition.

EXAMPLE 2

A granulated product of a surfactant having a particle diameter of 250 to 1,000 μm was prepared in a manner similar to Example 1 by using coconut oil fatty acid sodium salt (250 g) and starch (100 g). The granulated product (75 g) of the surfactant and powder (10 g) of sodium coconut oil fatty acid ethyl ester sulfonate were mixed with a nonaqueous base composed of ethylcarbitol (140 g) with a cellulose derivative (Metholose 90SH-4000, product of Shin-Etsu Chemical Co., Ltd.; 1.5 g) dispersed therein, and sorbitol (30 g) to obtain a substantially nonaqueous skin cleansing composition.

EXAMPLE 3

A granulated product of a surfactant having a particle diameter of 400 to 1,500 μm was prepared in a manner similar to Example 1 by using sodium monolauryl phosphate (230 g), bentonite (80 g) and sunflower oil (20 g). The granulated product (50 g) of the surfactant was mixed with a nonaqueous base composed of polyethylene glycol 400 (product of Sanyo Chemical industries, Ltd.; 180 g) with a cellulose derivative (Metholose 90SH-4000, product of. Shin-Etsu Chemical Co., Ltd.; 2.0 g) dispersed therein, and ethylcarbitol (30 g) to obtain a substantially nonaqueous skin cleansing composition.

EXAMPLE 4

A granulated product of a surfactant having a particle diameter of 50 to 600 μm was prepared in a manner similar to Example 1 by using sorbitan monolaurate (50 g), sodium alkylsulfate (100 g), lauryldimethylamine oxide (10 g), propyl cellulose (80 g) and silicone oil (Silicone KF-96, product of Shin-Etsu Chemical Co., Ltd.; 50 g).

The granulated product (20 g) of the surfactant was mixed with a nonaqueous base composed of dipropylene glycol (100 g) with an acrylic acid-alkyl methacrylate copolymer (Pemlene TR-1, product of B.F. Goodrich Company; 1.0 g) dispersed therein, and ethylcarbitol (100 g), and crystals (3 mm to 10 mm; 10 g) of coconut oil fatty acid sodium salt were further added to the resultant mixture to obtain a substantially nonaqueous skin cleansing composition.

EXAMPLE 5

A granulated product of a surfactant having a particle diameter of 100 to 1,000 μm was prepared in a manner similar to Example 1 by using sorbitan monolaurate (180 g) and starch (100 g). The granulated product (50 g) of the surfactant was mixed with ethylcarbitol (100 g) to obtain a substantially nonaqueous skin cleansing composition.

EXAMPLE 6

A granulated product of a surfactant having a particle diameter of 50 to 800 μm was prepared in a manner similar to Example 1 by using coconut oil fatty acid sodium salt (190 g) and polyvinyl alcohol (100 g).

The granulated product (70 g) of the surfactant was mixed with a nonaqueous base composed of polyethylene glycol 400 (product of Sanyo Chemical industries, Ltd.; 180 g) with a cellulose derivative (Metholose SEB-04T, product of Shin-Etsu Chemical Co., Ltd.; 2 g) dispersed therein to obtain a substantially nonaqueous skin cleansing composition.

COMPARATIVE EXAMPLE 1

An acrylic acid-alkyl methacrylate copolymer (Pemlene TR-1, product of B.F. Goodrich Company; 1.0 g) was dispersed in dipropylene glycol (100 g) to obtain a substantially nonaqueous composition.

COMPARATIVE EXAMPLE 2

Particles of a surfactant having a particle diameter of 100 to 800 μm were prepared in a manner similar to Example 1 by using coconut oil fatty acid sodium salt (80 g) and methyl cellulose (70 g).

The particles (50 g) of the surfactant were mixed with a base composed of glycerol (50 g) with a cellulose derivative (Metholose 60SH4000, product of Shin-Etsu Chemical Co., Ltd.; 1 g) dispersed therein, and purified water (50 g) to obtain a skin cleansing composition.

TEST EXAMPLE 1

The compositions obtained in Examples 1 to 6, and Comparative Examples 1 and 2 were evaluated as to a massaged feeling and cleanability upon use. The results are shown in Table 1.

Evaluation Method
(e) Massaged Feeling:

Each (2 g) of the compositions was applied to the lower inner arms of 10 Japanese women panelists of their twenties to thirties to massage them for at least 15 seconds. The composition was then washed out to organoleptically evaluate it as to the massaged feeling and cleanability in accordance with the following respective standards. An average score was found to express it as ○ where the average score was at least 2.5, Δ where the average score was 1.5 to 2.4, or X where the average score was at most 1.4.

(1) Massaged Feeling:

Felt a massaged feeling Score 3;

Somewhat felt a massaged feeling Score 2;

Felt no massaged feeling Score 1.

(2) Cleanability:

Had no sticky feel and gave a refreshed feeling Score 3;

Somewhat had a sticky feel Score 2;

Had a sticky feel Score 1.

TABLE 1

|  | Example | | | | | | Comp. Ex. | |
| --- | --- | --- | --- | --- | --- | --- | --- | --- |
|  | 1 | 2 | 3 | 4 | 5 | 6 | 1 | 2 |
| Massaged feeling | ○ | ○ | ○ | ○ | ○ | ○ | Δ | x |
| Cleanability | ○ | ○ | ○ | ○ | ○ | ○ | x | Δ |

All the substantially nonaqueous skin cleansing compositions obtained in Examples 1 to 6 gave a sufficient massaged feeling, had no sticky feel, gave a refreshed feeling and had excellent cleanability. In addition, they scarcely caused damage to and itch on the skin.

What is claimed is:

1. A substantially nonaqueous skin cleansing composition comprising:
   A) a granulated product having a particle diameter of 10–10,000 μm and consisting essentially of:
      i) solid surfactant particles, wherein said surfactant is selected from the group consisting of nonionic surfactants, amphoteric surfactants and anionic surfactants; and
      ii) a binder; and
   B) a nonaqueous base.
2. The substantially nonaqueous skin cleansing composition of claim 1, wherein said granulated product comprises 0.5–60% by weight of said composition.
3. The substantially nonaqueous skin cleansing composition of claim 1, which comprises ≦10% by weight of water.
4. The substantially nonaqueous skin cleansing composition of claim 1, wherein said nonaqueous base is selected from the group consisting of ethylene glycol monoethyl ether(ethylcarbitol), isoprene glycol, hexylene glycol, 1,2-pentanediol, polyethylene glycol, dipropylene glycol, ethylene glycol monobutyl ether, ethylene glycol monoethyl ether, 1,3-butylene glycol, 2-ethyl-1,3-hexanediol, diethylene glycol, propylene glycol, glycerol, sorbitol, tris(ethoxyethoxyethyl)phosphate and a mixture thereof.
5. The substantially nonaqueous skin cleansing composition of claim 1, wherein said non-aqueous base is a liquid at ordinary temperature and pressure.
6. The substantially nonaqueous skin cleansing composition of claim 1, wherein said binder is water-soluble.
7. The substantially nonaqueous skin cleansing composition of claim 1, wherein said binder is water-insoluble.
8. The substantially nonaqueous skin cleansing composition of claim 1, wherein said nonaqueous base comprises 40–99.5% by weight of the total weight of said composition.
9. A substantially nonaqueous skin cleansing composition comprising:
   A) a granulated product having a particle diameter of 10–10,000 μm and consisting essentially of:
      i) solid surfactant particles, wherein said surfactant is selected from the group consisting of nonionic surfactants, amphoteric surfactants and anionic surfactants;
      ii) a binder; and
      iii) an oil selected from the group consisting of sunflower oil, olive oil, silicone oil, volatile silicone oil and hardened castor oil; and
   B) a nonaqueous base.
10. The composition as claimed in claim 9, wherein said granulated product consists of said solid surfactant particles, said binder, and said oil.
11. The composition as claimed in claim 9, wherein said oil is selected from the group consisting of sunflower oil, olive oil, silicone oil, and hardened castor oil.
12. The composition as claimed in claim 9, wherein said oil is selected from the group consisting of sunflower oil, olive oil, volatile silicone oil and hardened castor oil.
13. The composition according to claim 1, wherein the surfactant comprises an anionic surfactant.

* * * * *